US009028801B2

(12) United States Patent
Ward et al.

(10) Patent No.: US 9,028,801 B2
(45) Date of Patent: May 12, 2015

(54) DIAGNOSIS OF NEURODEGENERATIVE DISEASES

(75) Inventors: Malcolm Andrew Ward, Shefford (GB); John Collinge, London (GB); Graham Stuart Jackson, Drayton (GB); Emma McGregor, London (GB); Nicola Louise Leeds, Tonbridge (GB); James Campbell, London (GB); Jules Arthur Westbrook, Middlesex (GB); Helen Louise Byers, London (GB)

(73) Assignees: Electrophoretics Limited, Cobham Surrey (GB); Medical Research Council, London (GB); University College London, London (GB)

( * ) Notice: Subject to any disclaimer, the term of this patent is extended or adjusted under 35 U.S.C. 154(b) by 1599 days.

(21) Appl. No.: 11/792,686

(22) PCT Filed: Dec. 7, 2005

(86) PCT No.: PCT/GB2005/004698
§ 371 (c)(1),
(2), (4) Date: May 15, 2008

(87) PCT Pub. No.: WO2006/061609
PCT Pub. Date: Jun. 15, 2006

(65) Prior Publication Data
US 2008/0213802 A1 Sep. 4, 2008

(30) Foreign Application Priority Data

Dec. 7, 2004 (GB) .................................... 0426859.5
Oct. 25, 2005 (GB) .................................... 0521762.5

(51) Int. Cl.
*A61B 5/145* (2006.01)
*G01N 33/48* (2006.01)
*C07K 14/805* (2006.01)
*C07K 14/75* (2006.01)
*C07K 14/705* (2006.01)
*G01N 33/68* (2006.01)

(52) U.S. Cl.
CPC .... *G01N 33/6896* (2013.01); *G01N 2800/2828* (2013.01); *G01N 2800/56* (2013.01); *G01N 2800/60* (2013.01)

(58) Field of Classification Search
None
See application file for complete search history.

(56) References Cited

U.S. PATENT DOCUMENTS

2002/0164661 A1* 11/2002 Clinton et al. ................ 435/7.21
2003/0152919 A1    8/2003 Roelens et al.

OTHER PUBLICATIONS

Pagnier et al., Biochimie, 57(1): 71-76, 1975. [abstract only].*
Pagnier et al., Biochimie, 57: 71-76, 1975.*
Sonati et al., Jornal de Pediatria (Rio), 84(4 Suppl):S40-51, Sep. 2008.*
Encarta World English Dictionary (North American Edition) 2009 [Online]. Retrieved on Dec. 30, 2009. Retrieved from: <http://encarta.msn.com/encnet/features/dictionary/DictionaryResults.aspx?lextype=3&search=valid>.*
Collins et al., J Clin Neurosci, 7(3):195-202, 2000.*
Gygi et al. PNAS, vol. 97 No. 17: 9390-9395, Aug. 2000.*
Guillaume, E. et al., A potential cerebrospinal fluid and plasmatic marker for the diagnosis of Creutzfeldt-Jakob disease; *Proteomics* 2003, 3, 1495-1499.
Choe, H. et al., Apolipoprotein E and other cerebrospinal fluid proteins differentiate ante mortem variant Creutzfeldt-Jakob disease from ante mortem sporadic Creutzfeldt-Jakob disease; *Electrophoresis* 2002, 23, 2242-2246.
International Search Report PCT/GB2005/004698; filed Dec. 7, 2007.
Emanuelli, Monica, et al., "Alpha-hemoglobin-stabilizing protein (AHSP) in hemolysis, elevated liver enzyme, and low platelet (HELLP) syndrome, intrauterine growth restriction (IUGR) and fetal death," Cell Stress and Chaperones, 2008, vol. 13, pp. 67-71.
Miele, Gino, et al., "A novel erythroid-specific marker of transmissible spongiform encephalopathies," Nature Medicine, Mar. 2001, vol. 7, No. 3, pp. 361-364.
UniProtKB/Swiss-Prot entry of Q9NZD4 (AHSP_HUMAN), Reviewed, Last modified Oct. 5, 2010, Version 76, 6 pages.
Hendrickson, E. et al., "High sensitivity multianalyte immunoassay using covalent DNA-labeled antibodies and polymerase chain reaction", Nucleic Acids Research, vol. 23, No. 3, 1995, pp. 522-529.
Weekes, J. et al., "Bovine dilated cardiomyopathy: Proteomic analysis of an animal model of human dilated cardiomyopathy", Electrophoresis, vol. 20, 1989, pp. 898-906.
Heinke, M.Y., et al.. "Changes in myocardial protein expression in pacing-induced canine heart failure", Electrophoresis, vol. 20, 1999, pp. 2086-2093.

* cited by examiner

*Primary Examiner* — Daniel E Kolker
*Assistant Examiner* — Stacey N MacFarlane
(74) *Attorney, Agent, or Firm* — Arent Fox LLP

(57) ABSTRACT

The invention relates to a method of diagnosis of vCJD in a diagnostic sample of a valid body tissue taken from a human subject, which comprises detecting an increased concentration of a protein in the diagnostic sample, compared with a sample of a control human subject, the protein being: beta-actin (SwissProt Acc. No. P60709), apolipoprotein A-IV precursor (SwissProt Acc. No. P06727); haptoglobin beta-chain consisting of residues 162-406 (SwissProt Acc. No. P00738); haemoglobin beta chain (SwissProt Acc. No. P02023); or alpha-1-antitrypsin (SwissProt Acc. No. P01009); or a decreased concentration of a protein in the diagnostic sample, compared with a sample of a control, normal human subject, the protein being plasma protease (C1) inhibitor precursor (SwissProt Acc. No. P05155); complement component 1, s sub-component (SwissProt Acc. No. P09871); butyrylcholinesterase precursor (SwissProt Acc. No. P06276); complement component C4B (SwissProt Acc. No. P01028); lumican (SwissProt Acc. No. P51884); alpha-fibrinogen precursor (SwissProt Acc. No. P02671); IGHG4 protein (Swiss Prot Acc. No. Q8TC63) or immunoglobulin lambda heavy chain. Other marker proteins are also disclosed.

10 Claims, 15 Drawing Sheets

Fig. 11  Control vs vCJD 8868 (P7)

Fig. 12 Control vs vCJD 14257

Fig.13 Control vs vCJD 27202 (P8)

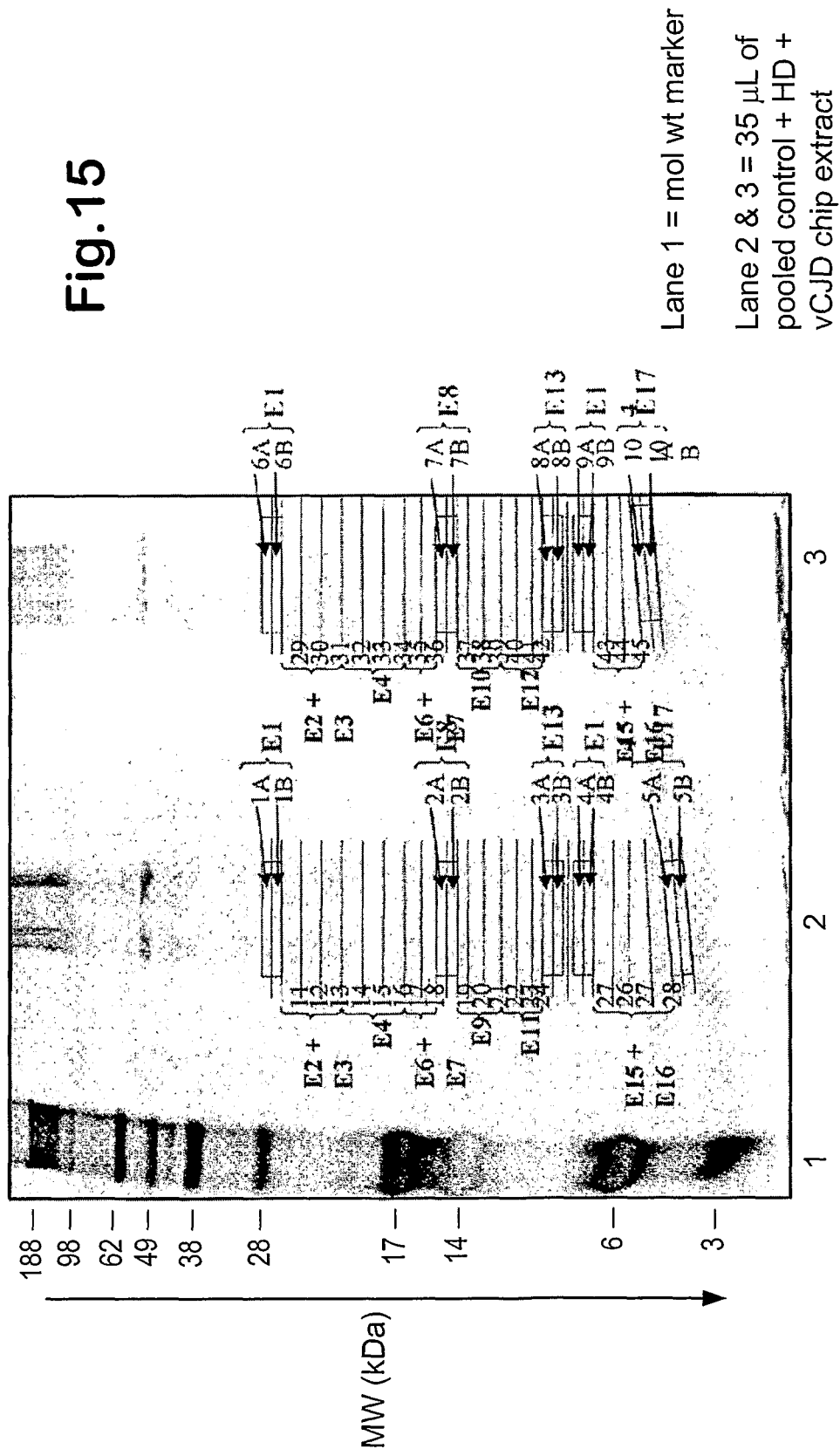

DIAGNOSIS OF NEURODEGENERATIVE DISEASES

BACKGROUND OF THE INVENTION

1. Field of the Invention

This invention relates to the diagnosis of neurodegenerative diseases, namely variant Creutzfeld-Jakob Disease (vCJD).

2. Description of the Related Art

The neuropathology of Creutzfeld-Jakob disease, as for other prion diseases, manifests itself as a characteristic spongiform appearance of the brain tissue, neuronal cell death in the central nervous system, accompanied by astrocyte proliferation and in some cases the deposition of amyloid plaques. Characteristic to all prion diseases is the accumulation in the brain of an altered, disease-associated form of the normal prion protein ($PrP^C$) represented as $PrP^{Sc}$. Four types of $PrP^{Sc}$ are associated with human prion disease. Of these, type 4 is associated only with variant CJD (vCJD) which came to light in the UK in 1996. It is believed to have arisen from the consumption by humans of BSE-infected beef. No samples from other prion diseases have shown a type 4 profile.

The difficulties of diagnosis of vCJD, have led to the need for further methods to be developed.

SUMMARY OF THE INVENTION

The invention provides the use of specified marker proteins and their partners in or for the diagnosis of vCJD. These marker proteins have been found to be differentially expressed in two dimensional electrophoresis and/or Surface Enhanced Laser Desorption Ionisation (SELDI) time of flight mass spectrometry profiling of plasma.

The marker proteins and their differential expression characteristics are as follows:

1A. Proteins present in an increased concentration in a vCJD sample compared with neurological and/or non-diseased controls: haptoglobin beta chain consisting of residues 162-406 (SwissProt Acc. No. P00738); haemoglobin beta chain (SwissProt No. P02023), alpha-1-antitrypsin (SwissProt Acc. No. P01009), beta-actin (SwissProt Acc. No. P60709), haemoglobin beta chain (SwissProt Acc. No. P02023) and apolipoprotein A-IV precursor (SwissProt Acc. No. P06727);

1B. Protein present in an decreased concentration in a vCJD sample, compared with a control: alpha-fibrinogen precursor (SwissProt Acc. No. P02671); IGHG4 protein (SwissProt Acc. No. Q8TC63); immunoglobulin lambda heavy chain; plasma protease (C1) inhibitor precursor (SwissProt Acc. No. P05155); complement component 1, s sub-component (SwissProt Acc. No. P09871), butyrylcholinesterase precursor (SwissProt Acc. No. P06276), complement component C4B (SwissProt Acc. No. P01028), and lumican (SwissProt Acc. No. P51884)

2. Proteins present in an increased or decreased concentration in a vCJD sample compared with a control:

| Protein ID | Swiss Prot Accession # |
| --- | --- |
| Transthyretin | P02766 |
| Haptoglobin | P00738 |
| Apolipoprotein C-III | P02656 |
| Vitronectin precursor | P04004 |
| Hemoglobin beta chain | P02025 |
| IgG lambda chain C | P01842 |
| IgG kappa chain C | P01834 |
| Serum Albumin | P02768 |
| Apolipoprotein A-1 | P02647 |
| Actin | P62736 |
| alpha-Fetuin | P02765 |

Thus, the invention includes specifically:

1. A method of diagnosis of vCJD in a diagnostic sample of a valid body tissue, especially a body fluid, taken from a human subject, which comprises detecting an increased concentration of a protein in the diagnostic sample, compared with a sample of a non neurologically diseased control, normal human subject, the protein being:
haptoglobin beta-chain consisting of residues 162-406 (SwissProt Acc. No. P00738);
haemoglobin beta chain (SwissProt Acc. No. P02023);
alpha-1-antitrypsin (SwissProt Acc. No. P01009);
beta actin (SwissProt Acc. No. P60709) or
apolipoprotein A-IV precursor (SwissProt Acc. No. P06727)
or a decreased concentration of a protein in the diagnostic sample, compared with a sample of a non-neurologically diseased control, normal human subject, the protein being alpha-fibrinogen precursor (SwissProt Acc. No. P02671);
IGHG4 protein (Swiss Prot Acc. No. Q8TC63) or
immunoglobulin lambda heavy chain.

2. A method of diagnosis of vCJD in a diagnostic sample of a valid body tissue, especially a body fluid, taken from a human subject, which comprises detecting an increased concentration of a protein in the diagnostic sample, compared with a sample of a control, normal human subject, the protein being selected from:

| Protein ID | Swiss Prot Accession # |
| --- | --- |
| Transthyretin | P02766 |
| Haptoglobin | P00738 |
| Apolipoprotein C-III | P02656 |
| Vitronectin precursor | P04004 |
| Hemoglobin beta chain | P02025 |
| IgG lambda chain C | P01842 |
| IgG kappa chain C | P01834 |
| Serum Albumin | P02768 |
| Apolipoprotein A-1 | P02647 |
| Actin | P62736 |
| alpha-Fetuin | P02765 |

3. A method of diagnosis which distinguishes vCJD from other neurological disease in a diagnostic sample of a valid body tissue, especially a body fluid, taken from a human subject, which comprises detecting an increased or decreased concentration of a protein in the diagnostic sample, compared with a reference sample, the protein being haemoglobin beta chain (SwissProt Acc. No. P02023), which is increased in a vCJD sample compared with other neurological disease; or a protein selected from: plasma protease (C1) inhibitor precursor (SwissProt Acc. No. P05155); complement component 1, s sub-component (SwissProt Acc. No. P09871), butyrylcholinesterase precursor (SwissProt Acc. No. P06276), complement component C4B (SwissProt Acc. No. P01028), and lumican (SwissProt Acc. No. P51884), which is decreased in a vCJD sample compared with other neurological disease.

The marker protein can be present in the body tissue in any biologically relevant form, e.g. in a glycosylated, phosphorylated, multimeric or precursor form.

Although there is a high degree of confidence in the identification of the marker proteins specified above, the invention can be defined alternatively in terms of the proteins within the differentially expressed spots on a two dimensional electrophoretic gel, namely those identified in FIGS. 2 to 5 herein, without regard to the names and database identifications given above.

DEFINITIONS

The term "differentially expressed" in the context of 2 dimensional gel electrophoresis means that the stained protein-bearing spots are present at a higher or lower optical density in the gel from the sample taken for diagnosis (the "diagnostic sample") than the gel from a control or other comparative sample, and in the context of SELDI-TOF means that the protein peak is at a higher or lower intensity in the mass spectrogram from the sample taken for diagnosis (the "diagnostic sample") than the mass spectrogram from a control or other comparative sample. It follows that the proteins are present in the plasma of the diagnostic sample at a higher or lower concentration than in the control or other comparative sample in the same direction of differential expression seen in S dimensional gel electrophoresis and SELDI-TOF.

The term "control" refers to a human subject not suffering from vCJD.

The terminology "increased/decreased concentration . . . compared with a sample of a control" does not imply that a step of comparing is actually undertaken, since in many cases it will be obvious to the skilled practitioner that the concentration is abnormally high. Further, when the stage of vCJD progression is being monitored progressively, the comparison made can be with the concentration previously seen in the same subject earlier in the progression of the disease.

The term "binding partner" includes a substance that recognises or has affinity for the marker protein. It may or may not itself be labelled.

The term "marker protein" includes all biologically relevant forms of the protein identified.

The term "diagnosis", as used herein, includes determining whether vCJD is present or absent and also includes determining the stage to which it has progressed. The diagnosis can serve as the basis of a prognosis as to the future outcome for the patient.

The term "valid body tissue" means any tissue in which it may reasonably be expected that a marker protein would accumulate in relation to vCJD. While it will principally be a body fluid, it also includes brain or nerve tissue, tonsil, spleen and other lymphoreticular tissue, it being understood that the diagnosis can be made either pre-mortem or post mortem.

BRIEF DESCRIPTION OF THE FIGURES

FIG. 15 is an image of a silver stained gel of the material extracted from depleted plasma WCX CM10 chips, as described in Example 2.

DESCRIPTION OF PREFERRED EMBODIMENTS

Figure 1:
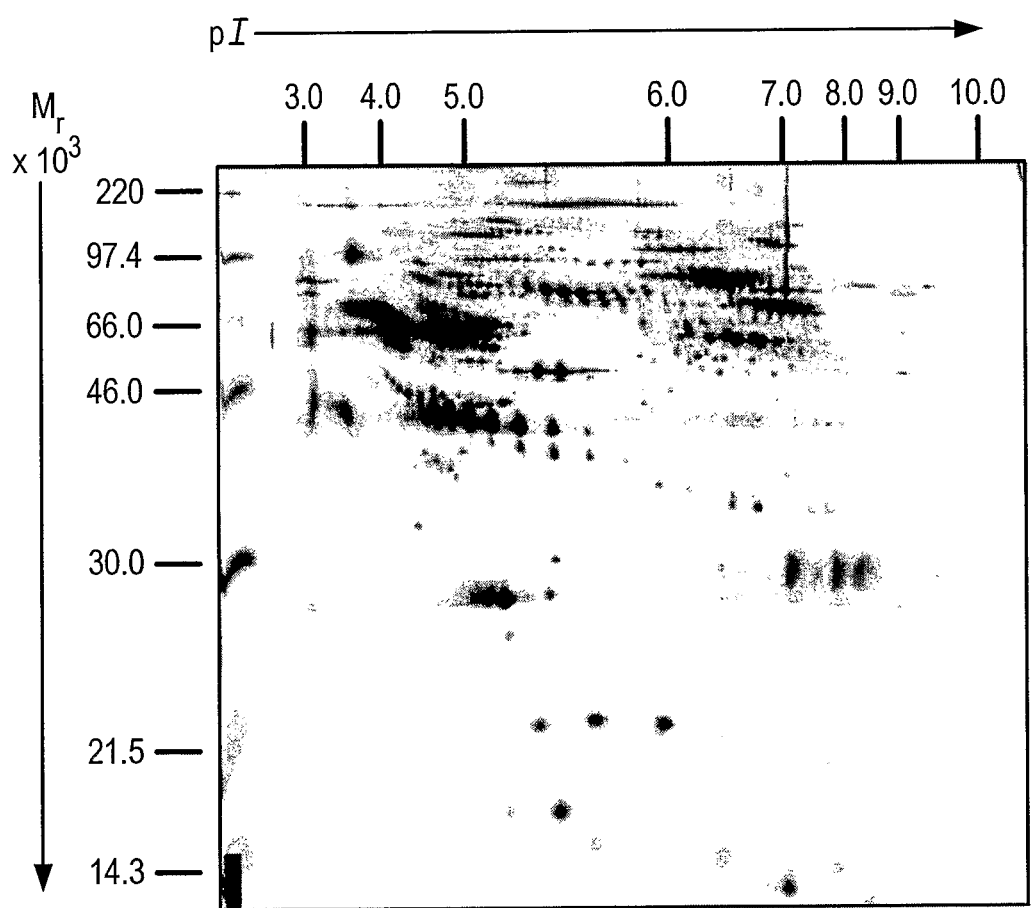
FIG. 1 is a photograph of a typical two dimensional gel performed for analytical purposes, by the method described in Example 1 below, on a sample derived from a vCJD patient. The molecular weight (relative molecular mass) is shown on the ordinate in kiloDaltons. Molecular weight markers are shown at the left-hand side. The isoelectric point (pI) is shown on the ordinate, increasing from left to right.
Figure 2:
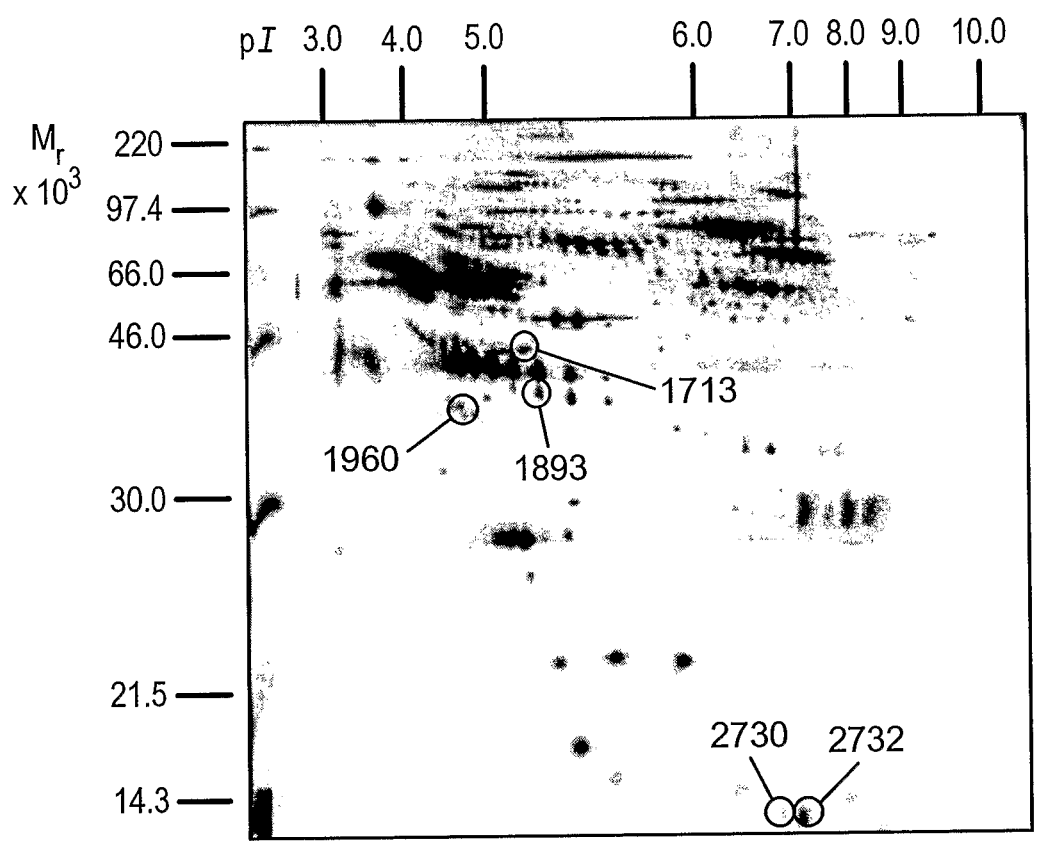
FIG. 2 is a photograph of a similar gel, but marked with spots 1713, 1893, 1960, 2730 and 2732, explained in detail in Example 1. Spot 1960, although a marker protein for HD (not vCJD) is shown here for convenience, since it does appear in vCJD patients, at about the same level as in a control.
Figure 3:
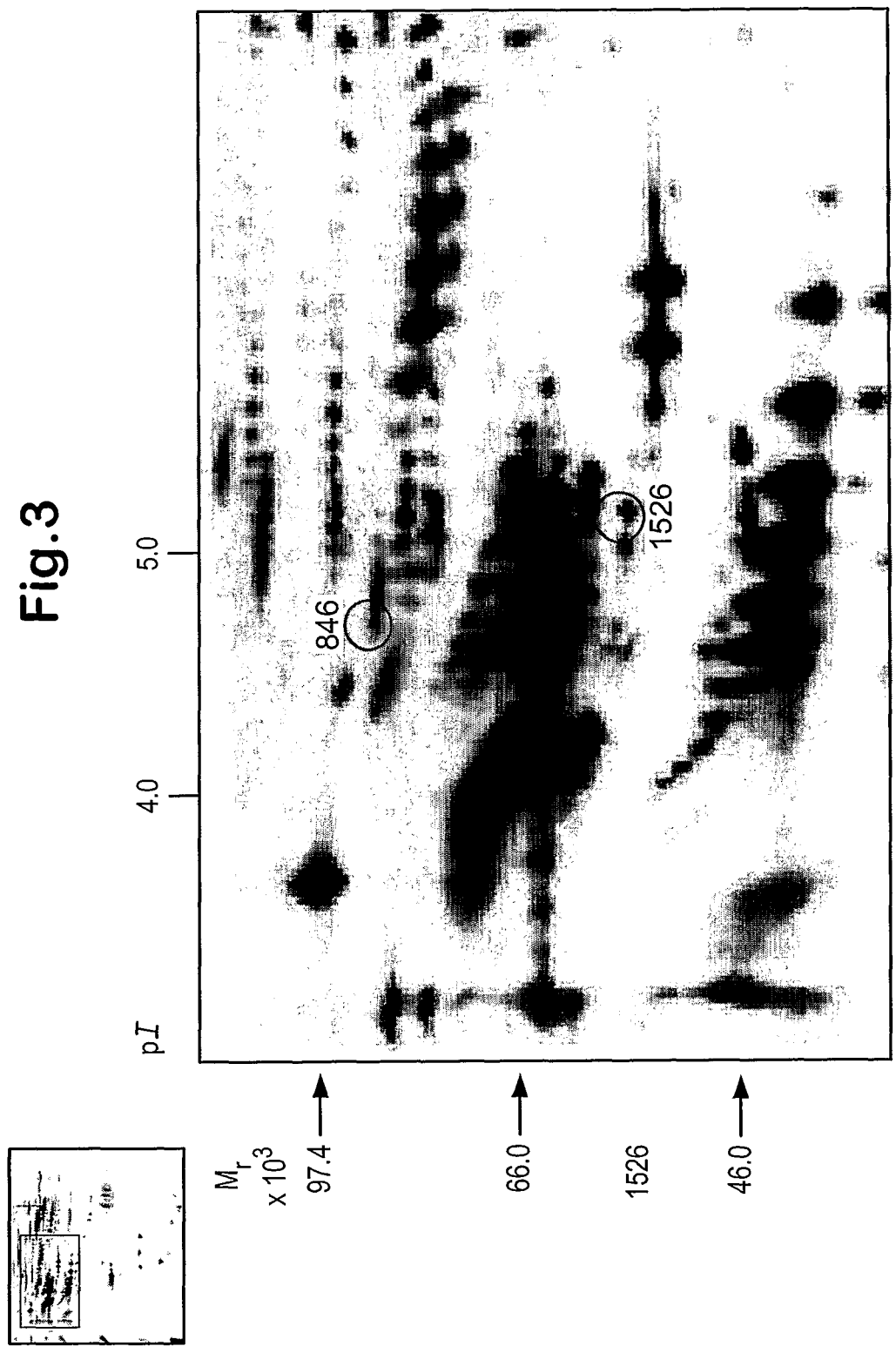
FIG. 3 is a photograph enlarged to show a portion of the gel of FIG. 1 and the spots 846 and 1526.
Figure 4:
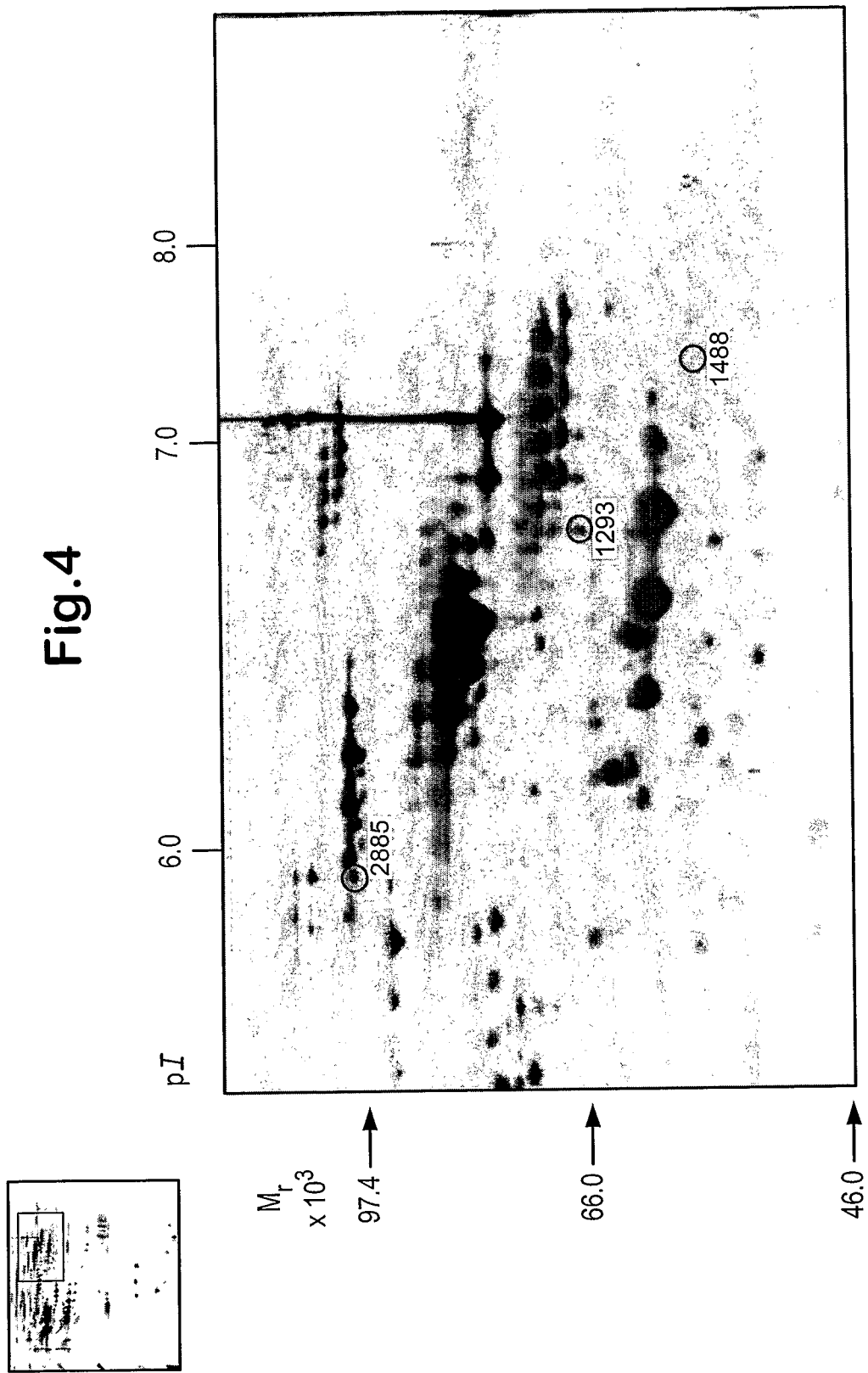
FIG. 4 is a photograph enlarged to show another portion of the gel of FIG. 1 and the spot 1488. The spots 1293 and 2885 are also shown, but they were not further pursued, as explained in Example 1.
Figure 5:
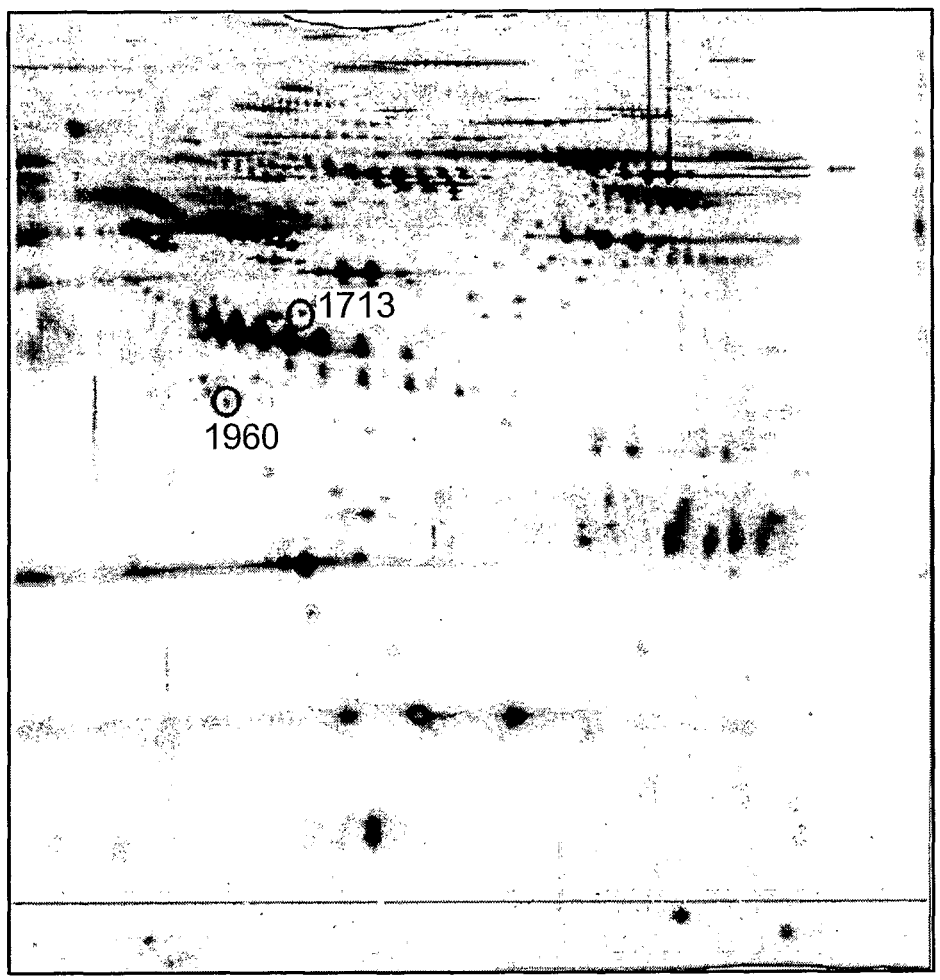
FIG. 5 is similar to FIG. 2, but showing spots 1713 and 1960 in a sample derived from an HD patient.

A preferred method of diagnosis comprises performing a binding assay for the marker protein. Any reasonably specific binding partner can be used. Preferably the binding partner is labelled. Preferably the assay is an immunoassay, especially between the marker and an antibody that recognises the protein, especially a labelled antibody. It can be an antibody raised against part or all of it, most preferably a monoclonal antibody or a polyclonal anti-human antiserum of high specificity for the marker protein.

Thus, the marker proteins described above are useful for the purpose of raising antibodies thereto which can be used to detect the increased or decreased concentration of the marker proteins present in a diagnostic sample. Such antibodies can be raised by any of the methods well known in the immunodiagnostics field.

The antibodies may be anti- to any biologically relevant state of the protein. Thus, for example, they could be raised against the unglycosylated form of a protein which exists in the body in a glycosylated form, against a more mature form of a precursor protein, e.g. minus its signal sequence, or against a peptide carrying a relevant epitope of the marker protein.

The sample can be taken from any valid body tissue, especially body fluid, of a (human) subject, but preferably blood, plasma or serum. Other usable body fluids include cerebrospinal fluid (CSF), urine and tears.

According to another embodiment of the invention, the diagnosis is carried out pre- or post mortem on a body tissue of neurological origin relevant to vCJD such as from the brain or nerves, tonsil, spleen or other lymphoreticular tissue. The tissue is pre-treated to extract proteins therefrom, including those that would be present in the blood of the deceased, so as to ensure that the relevant marker proteins specified above will be present in a positive sample. For the purposes of this patent specification, such an extract is equivalent to a body fluid.

By way of example, brain tissue is dissected and subsections solubilised by methods well established in the art such as mechanical disruption in a phosphate buffered saline, in a ratio of about 100 mg tissue to 1 ml buffer. Where desirable chaotropic salts such as guanidinium hydrochloride or sodium dodecylsulphate may be included to inactivate the infectious prion agent so long as this does not interfere with subsequent detection of the vCJD biomarkers.

The preferred immunoassay is carried out by measuring the extent of the protein/antibody interaction. Any known method of immunoassay may be used. A sandwich assay is preferred. In this method, a first antibody to the marker protein is bound to the solid phase such as a well of a plastics microtitre plate, and incubated with the sample and with a labelled second antibody specific to the protein to be assayed. Alternatively, an antibody capture assay could be used. Here, the test sample is allowed to bind to a solid phase, and the anti-marker protein antibody is then added and allowed to bind. After washing away unbound material, the amount of antibody bound to the solid phase is determined using a labelled second antibody, anti- to the first.

In another embodiment, a competition assay is performed between the sample and a labelled marker protein or a peptide derived therefrom, these two antigens being in competition for a limited amount of anti-marker protein antibody bound to a solid support. The labelled marker protein or peptide thereof could be pre-incubated with the antibody on the solid phase, whereby the marker protein in the sample displaces part of the marker protein or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

The label is preferably an enzyme. The substrate for the enzyme may be, for example, colour-forming, fluorescent or chemiluminescent.

The binding partner in the binding assay is preferably a labelled specific binding partner, but not necessarily an antibody. For example, when the marker protein is alpha-1-antitrypsin, the specific binding partner can be trypsin. The binding partner will usually be labelled itself, but alternatively it may be detected by a secondary reaction in which a signal is generated, e.g. from another labelled substance.

It is highly preferable to use an amplified form of assay, whereby an enhanced "signal" is produced from a relatively low level of protein to be detected. One particular form of amplified immunoassay is enhanced chemiluminescent assay. Conveniently, the antibody is labelled with horseradish peroxidase, which participates in a chemiluminescent reaction with luminol, a peroxide substrate and a compound which enhances the intensity and duration of the emitted light, typically 4-iodophenol or 4-hydroxycinnamic acid.

Another preferred form of amplified immunoassay is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

Alternatively, the diagnostic sample can be subjected to two dimensional gel electrophoresis to yield a stained gel and the increased or decreased concentration of the protein detected by an increased an increased or decreased intensity of a protein-containing spot on the stained gel, compared with a corresponding control or comparative gel. The relevant spots, diseases identified and differential expression are those listed in Table 1 below. The invention includes such a method, independently of the marker protein identification given above and in Table 2.

The diagnosis does not necessarily require a step of comparison of the concentration of the protein with a control, but it can be carried out with reference either to a control or a comparative sample. Thus the invention can be used to determine the stage of progression of vCJD if desired by comparison of protein levels with results obtained earlier from the same patient or by reference to standard values that are considered typical of the stage of the disease. In this way, the invention can be used to determine whether, for example after treatment of the patient with a drug or candidate drug, the disease has progressed or not. The result can lead to a prognosis of the outcome of the disease.

The invention further includes the use for a diagnostic (and thus possibly prognostic) or therapeutic purpose of a partner material which recognises, binds to or has affinity for a marker protein specified above and/or represented by a differentially expressed two dimensional gel electrophoretic spot shown in any of FIGS. 2 to 5 herein, or the differentially expressed SELDI peaks at MW 3223 Da, MW4132 Da, MW4340 Da, MW4490 Da, MW6243 Da, MW 7533 Da, MW 8644 Da, MW 8856 Da, MW 8868 Da, MW 14257 Da, MW 27202 Da. Thus, for example, antibodies to the marker proteins, appropriately humanised where necessary, may be used to treat vCJD and HD. The partner material will usually be an antibody and used in any assay-compatible format, conveniently an immobilised format, e.g. micro- or nanoparticle beads or a glass, silicone or nitrocellulose chip. Either the partner material will be labelled or it will be capable of interacting with a label.

The invention further includes a kit for use in a method of diagnosis, which comprises a partner material, as described above, in an assay-compatible format, as described above, for interaction with a protein present in the diagnostic sample.

The diagnosis can be based on the differential expression of one, two, three or more of the marker proteins. Further, it can be part of a wider diagnosis in which one or more additional diseases are diagnosed in addition to vCJD. Accordingly vCJD can be diagnosed along with at least one other disease, which may or may not be neurological, in the same sample of body fluid, by a method which includes detecting an increased concentration of another protein in the diagnostic sample, compared with a sample of a control, normal human subject. These other disease(s) can be any which are diagnosable in a body fluid. They may be neurological, e.g. another transmissible spongiform encephalopathy, Alzheimer's disease, Huntington's disease, Parkinson's Disease, meningitis, but are not necessarily neurological, for example toxic shock syndrome, MRSA or Celiac disease.

Thus, in particular, it is contemplated within the invention to use an antibody chip or array of chips, capable of diagnosing one or more proteins that interact with that antibody.

The following Examples illustrate the invention.

Example 1

Ten plasma samples were taken from patients (4 female, 6 male) who were diagnosed with variant CJD (vCJD), ten from patients (7 female, 3 male) diagnosed by genetic testing as having Huntington's Disease (HD) serving as a neurological disease control and ten from non-diseased controls, i.e. normal patients (8 female, 2 male) not having any neuropathological symptoms.

Albumin and IgG were removed from the samples using a kit supplied by Amersham Biosciences UK Ltd. This kit contains an affinity resin containing antibody that specifically removes albumin and IgG directly from whole human serum and plasma samples. It is claimed that more than 95% albumin and more than 90% IgG removal from 15 µl human serum/plasma can be achieved, thereby increasing the resolution of lower abundance proteins in subsequent electrophoresis. A microspin column is used, through which the unbound protein is eluted.

Depletion was carried out according to the manufacturer's instructions using a starting volume of 15 µl of crude plasma sample. The resin was added to the plasma, the mixture incubated with shaking, transferred to a microspin column, centrifuged and the filtrate collected. The resulting depleted sample was concentrated and de-salted by acetone precipitation (as recommended in the instructions of the kit). The acetone was decanted and the pellets were re-suspended in standard 2-D gel lysis buffer (9.5 M urea, 2% CHAPS, 1% DTT, 0.8% Pharmalyte, pH 3-10, protease inhibitors (1 tablet/10 ml lysis buffer) (Roche). This suspension was used for the two dimensional gel electrophoresis.

Two dimensional gel electrophoresis was performed according to J. Weekes et al., Electrophoresis 20: 898-906 (1999) and M. Y. Heinke et al., Electrophoresis 20: 2086-2093 (1999), using 18 cm immobilised pH 3-10 non-linear gradient strips (IPGs). The second dimension was performed using 12% T SDS polyacrylamide gel electrophoresis. For the initial analysis, the gels were loaded with 75 micrograms of protein. The gels were silver-stained with the analytical OWL silver stain (Insight Biotechnologies, UK).

Quantitative and qualitative image analysis was performed using the software Progenesis™ Workstation, version 2003.02 (Nonlinear Dynamics Ltd.). The images were processed through the automatic wizard for spot detection, warping and matching. Thereafter, all images underwent extensive manual editing and optimal matching to the reference gel (>80% per gel). Following background subtraction and normalisation to total spot volume, protein spot data was exported to Excel for quantitative statistical analysis and comparisons of qualitative changes.

The student t-test, at the 95% confidence interval, was performed for every protein spot that could be compared between the samples from the diseased patients and the controls and which was present in at least 60% of the gels of each group, i.e. at least 6. A log transformation was performed, since this gave a more normal distribution, thus better meeting the assumptions of this test as applied to independent samples.

The spots for which a significant increase or decrease was observed in comparisons between the three groups are shown in FIGS. 2 to 5 and listed in Table 1.

TABLE 1

| Spot No. | FIG. | Quantitative change (Increase/Decrease in intensity of spot in comparisons between vCJD, HD and control samples). | p value (t-test) | No. samples in which spot seen vCJD/HD/Control |
|---|---|---|---|---|
| 1893 | 2 | Inc. vCJD vs. Control | 0.001 | 10/10/10 |
| 2732 | 2 | Inc. vCJD vs. Control | 0.001 | 10/10/10 |
| 2732 | 2 | Inc. vCJD vs. Neurological Control | 0.002 | 10/10/10 |
| 1713 | 2 | Inc. vCJD vs. Control | 0.003 | 8/10/6 |
| 1713 | 5 | Inc. HD vs. Control | 0.000065 | 8/10/6 |
| 1526 | 3 | Inc. vCJD vs. Control | 0.003 | 10/10/8 |
| 1488 | 4 | Dec. vCJD vs. Control | 0.003 | 7/10/10 |
| 2730 | 2 | Inc. vCJD vs. Control | 0.003 | 10/9/10 |
| 846 | 3 | Dec. vCJD vs. Neurological Control | 0.006 | 9/8/6 |
| 1960 | 5 | Inc. HD vs. Control | 0.004 | 10/10/10 |

Quantitative changes were seen in two other spots (1293 and 2885) on the analytical gels, but not on the preparative gels (see below). These were both in the vCJD vs. neurological control (HD) comparison. Spot 1293 was decreased and 2885 increased in vCJD versus neurological control (HD).

It will be seen that spot 1713 is one to which particularly high confidence in the results can be attached in relation to the increase in its intensity in the neurological control (HD) samples versus controls. This spot also showed an increase in the vCJD vs. control comparison.

Spots 1893, 2732, 1526 and 2730 showed increases in the vCJD versus controls comparison. Spot 2732 also showed an increase in the vCJD samples compared with neurological control (HD).

Spot 846 was decreased in the vCJD samples compared with neurological control (HD).

For preparative purposes, further two dimensional gels were then made by the same method, by pooling all samples within each experimental group and loading the gels with 400 micrograms of protein. There were thus three gels prepared, one for each group, which were silver stained, using PlusOne silver stain (Amersham Pharmacia Biosciences UK Ltd.).

Normally, the spots were excised from the preparative gels in which they were elevated in intensity, but where this was not possible i.e. where spots were decreased in intensity in vCJD, they were excised from another gel. After in-gel reduction, alkylation and digestion of the excised material with trypsin, the peptides produced were extracted and subsequently analysed by LC/MS/MS. This procedure involves separation of the peptides by reversed phase HPLC, followed by electrospraying to ionise the sample, as it enters a tandem mass spectrometer. The mass spectrometer records the mass to charge ratio of the peptide precursor ions, which are then individually selected for fragmentation via collisionally induced dissociation (CID). This so-called MS/MS scan allows for the sequence of the peptide to be determined. For each sample, therefore, the data set includes accurately determined molecular weights for multiple peptides present, accompanied by corresponding sequence information. This is then used to identify the protein by searching databases. In the present case, the Mascot search algorithm was used against the National Center for Biotechnology Information (NCBI) non-redundant protein (nr) and SWISS-PROT databases.

The results of the identification are shown in Table 2. All the spots of Table 1 that were differentially expressed on the gel were identified as known proteins.

The Table shows the geninfo (gi) numbers of the NCBI database and SwissProt Accession numbers.

In some instances more than one protein was identified, which signifies that the spot excised contained a mixture of proteins, at least one of which was differentially expressed on the gel. The proteins identified in the database had different molecular weights and isoelectric points, lower or higher, from those evident on the gel. This is entirely usual and can be accounted for by the protein within the gel spot having undergone enzymatic or chemical cleavage or by having been post-translationally modified such as by glycosylation, phosphorylation or the addition of lipids.

As between spots 2730 and 2732, which relate to forms of the same protein, 2732 is of slightly higher pI and reference thereto should be understood accordingly.

TABLE 2

| Spot No. | MW (DA) from gel | pI from gel | Human protein identified | NCBI nr and SwissProt Acc. No. | No. peptides matched (% coverage) |
|---|---|---|---|---|---|
| 1893 | 35473 | 5.30 | Haptoglobin beta chain* | gi/67586 P00738 | 15 (47%) |

TABLE 2-continued

| Spot No. | MW (DA) from gel | pI from gel | Human protein identified | NCBI nr and SwissProt Acc. No. | No. peptides matched (% coverage) |
|---|---|---|---|---|---|
| 2732 | 13387 | 7.07 | Haemoglobin beta chain | gi/4504349 P02023 | 13 (84%) |
| 1713 | 43108 | 5.19 | Beta actin | gi/4501885 P60709 | 14 (47%) |
|  |  |  | Apolipoprotein A-IV precursor | gi/4502151 P06727 | 7 (26%) |
| 1526 | 53638 | 4.74 | Alpha-1-antitrypsin | gi/177827 P01009 | 3 (9%) |
| 1488 | 56468 | 7.32 | Alpha-fibrinogen precursor | gi/182424 P02671 | 4 (7%) |
|  |  |  | IGHG4 protein | gi/19684073 Q8TC63 | 4 (11%) |
|  |  |  | Immunoglobulin lambda heavy chain | gi/2765425 | 5 (14%)** |
| 2730 | 13470 | 6.88 | Haemoglobin beta chain | gi/4504349 P02023 | 10 (84%) |
| 846 | 93995 | 4.76 | Plasma protease (C1) inhibitor precursor | gi/179619 P05155 | 5 (11%) |
|  |  |  | Complement component 1, s sub-component | gi/34785163PP09871 | 2 (5%) |
|  |  |  | Butyrylcholinester-ase precursor | gi/4557351 P06276 | 2 (5%) |
|  |  |  | Complement component C4B | gi/187771 P01028 | 1 (6%) |
|  |  |  | Lumican | gi/642534 P51884 | 1 (4%) |

Footnotes to Table 2
*the haptoglobin beta-chain consisting of residues 162-406 of the database sequence, which is formed by enzymatic cleavage of the precursor; this protein is glycosylated in plasma
**including 2 unique peptides Example 2

Discovery of vCJD Biomarkers by SELDI-TOF Mass Spectrometry

A second set of vCJD biomarkers were revealed using Surface Enhanced Laser Desorption Ionisation (SELDI) time of flight mass spectrometry. Experiments to establish the identity of these new candidates are also described.

1.1 Sample Preparation for SELDI Discovery

The plasma samples used in Example 1 from clinically confirmed cases of vCJD (n=10), neurological controls (HD) (n=10) and non-diseased control (n=10) patients were collected from the MRC Prion unit. Two microliters of each of the depleted samples were diluted in 3 ul of lysis buffer containing 9.5 M urea, 2% CHAPS, 0.8% pharmalyte pH 3-10, 1% DTT and protease inhibitor and undepleted samples were diluted in the same ratio using the above lysis buffer without pharmalyte.

1.2 Plasma Depletion

Consistent with the previous 2DE study, Albumin and IgG were removed from the plasma using a commercially available resin (GE Healthcare). This kit is antibody based and contains a resin that specifically removes albumin and IgG directly from whole human serum and plasma samples. It is claimed that >95% albumin and >90% IgG from 15 µl human serum/plasma can be achieved, thereby increasing the resolution of lower abundance proteins. A microspin column is used through which the unbound protein is eluted.

Depletion was carried out according to the manufacturer's instructions using a starting volume of 15 µl of crude plasma sample. The resulting depleted sample was acetone precipitated (as recommended in the instructions of the kit) and re-suspended in standard 2DE lysis buffer (as indicated in section 2.2 above)

1.3 Surface Enhanced Laser Desorption Ionisation (SELDI) Mass Spectrometry

Profiling of depleted plasma samples were performed using an eight spot strong anion exchange (Q10) protein chip array and profiling of undepleted plasma were performed using both the eight spot Q10 and weak cation exchange (CM10) protein chip arrays. All samples were run in duplicate and in a randomised manner. Essentially, all the Q10 and CM10 chips were equilibrated four times in the appropriate wash buffer. For Q10 chips, 100 mM Tris HCl pH 9.0 was used as the wash buffer and for CM10 the wash buffer was 50 mM sodium acetate pH 7.5. 5 µl of the diluted samples were applied to each spot and this was then incubated in a humidity chamber for 45 minutes. Samples were carefully removed and the chips were washed four times in the appropriate wash buffer and one wash with 18.2 MΩ water. 0.6 µl matrix solution containing 20 mg/ml sinnapinic acid (Ciphergen) in 50% acetonitrile (Fisher Scientific) and 0.5% trifluroacetic acid was applied twice to each spots. Data acquisition was performed using a PBS-II reader (Ciphergen Biosystems). Spectra were acquired using a summation of 155 shots with a laser intensity of 200, detector sensitivity of 8 and a focus mass m/z 25000. Baseline subtraction and normalisation on total ion count were performed on all the spectra. Internal calibration of each spectra was undertaken using a minimum of 2 peaks in each spectrum.

Figure 6:
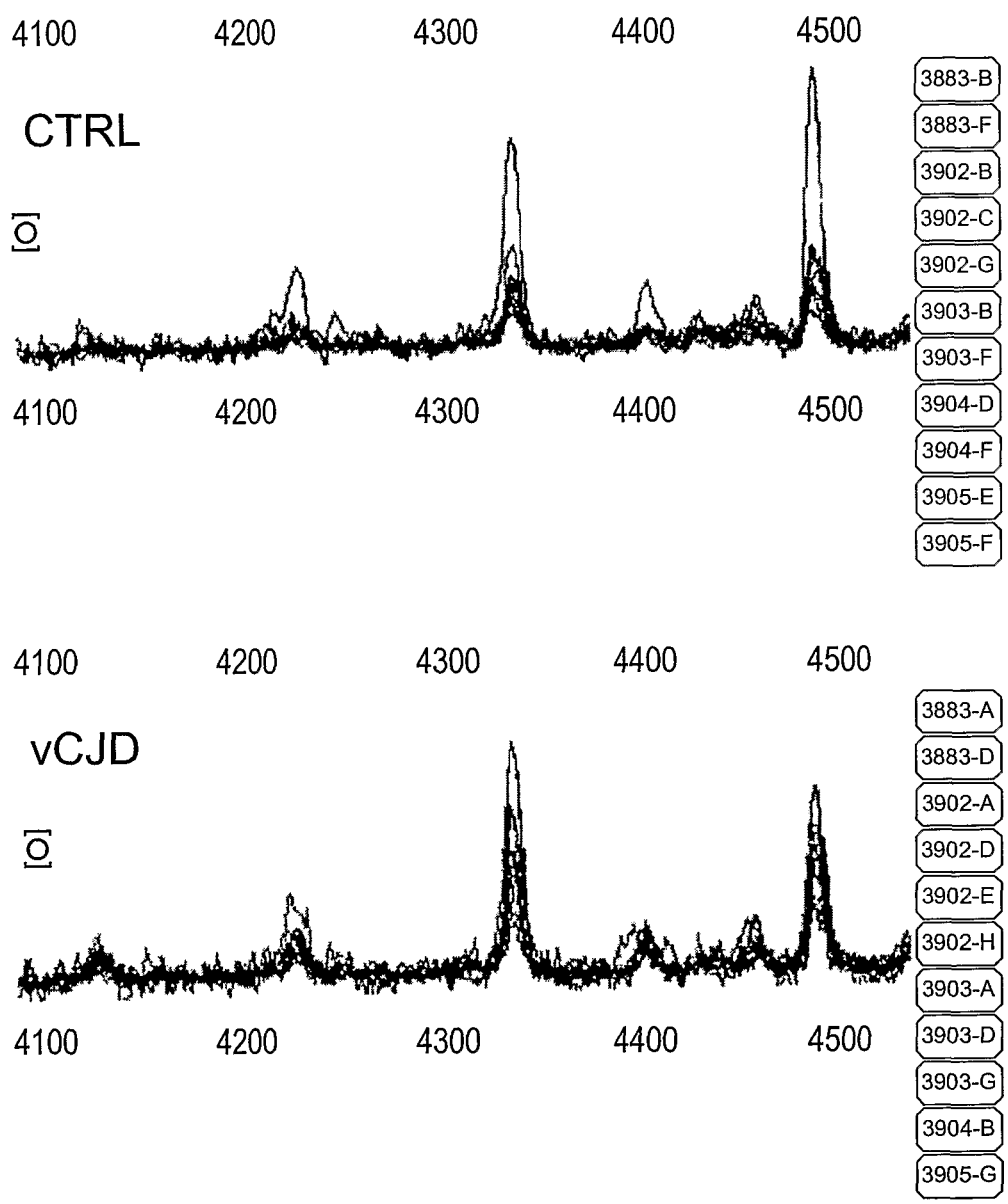
FIGS. 6 to 13 are SELDI traces, as described more fully in Example 2.
Figure 7:
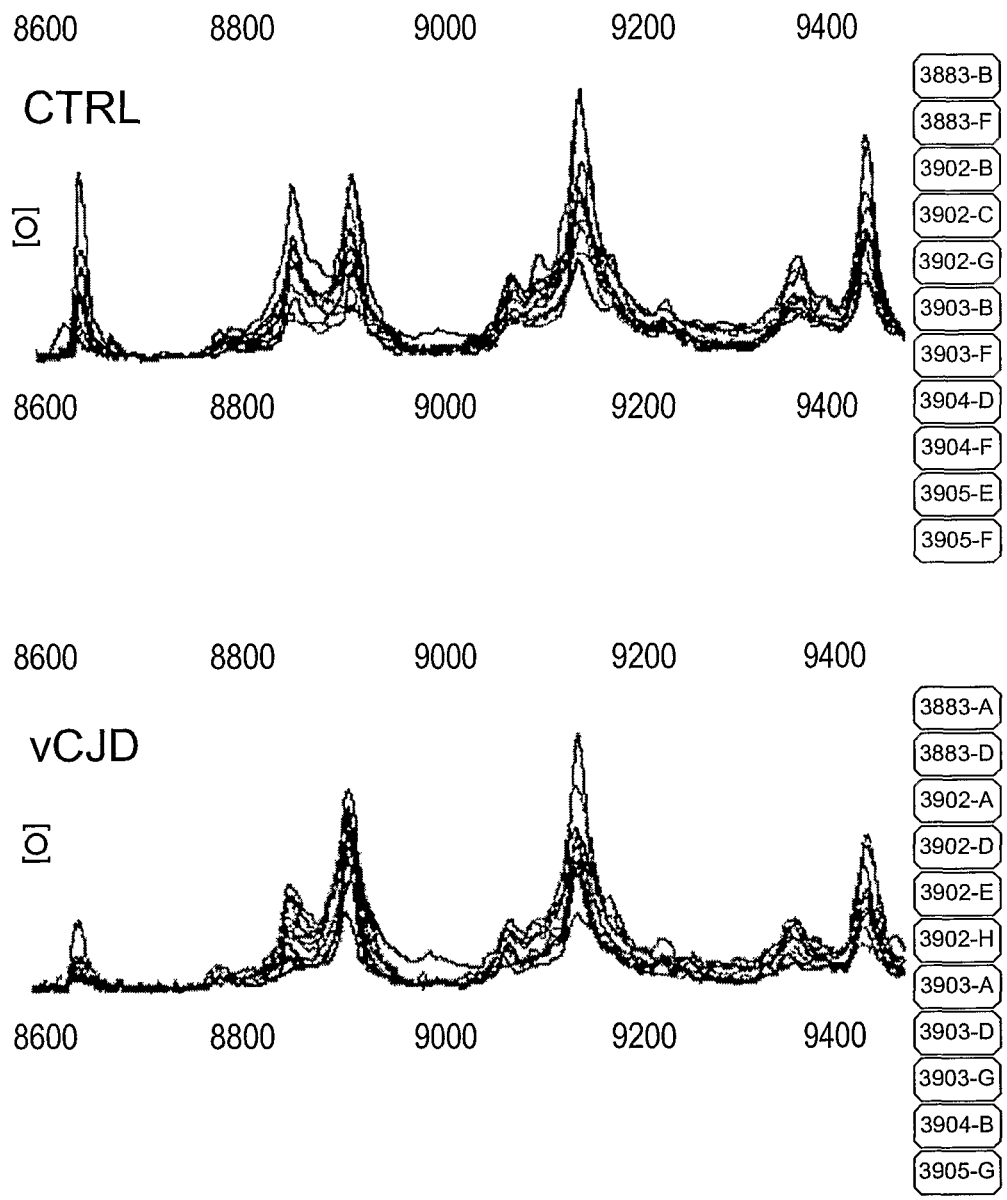
Figure 8:
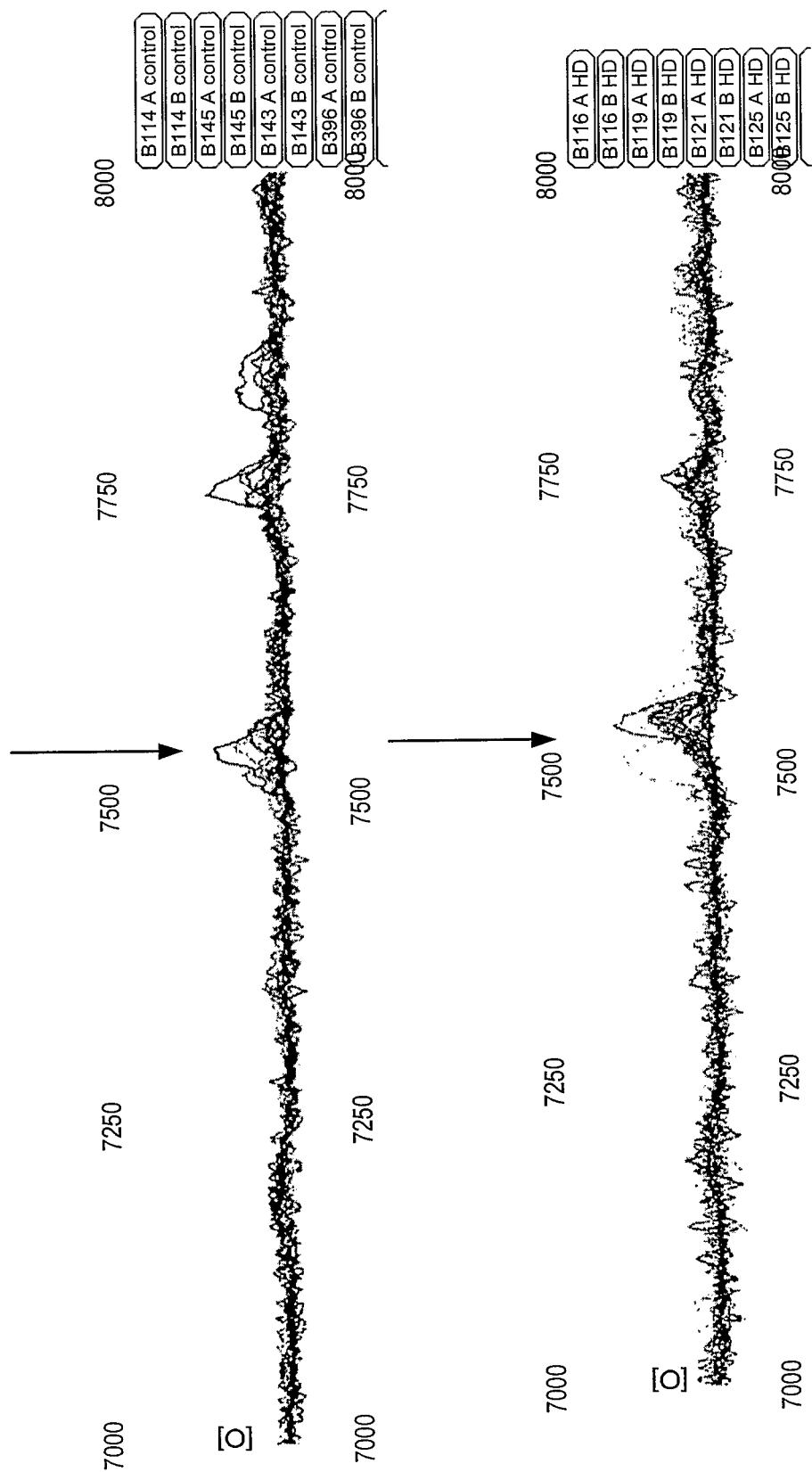
Figure 9:
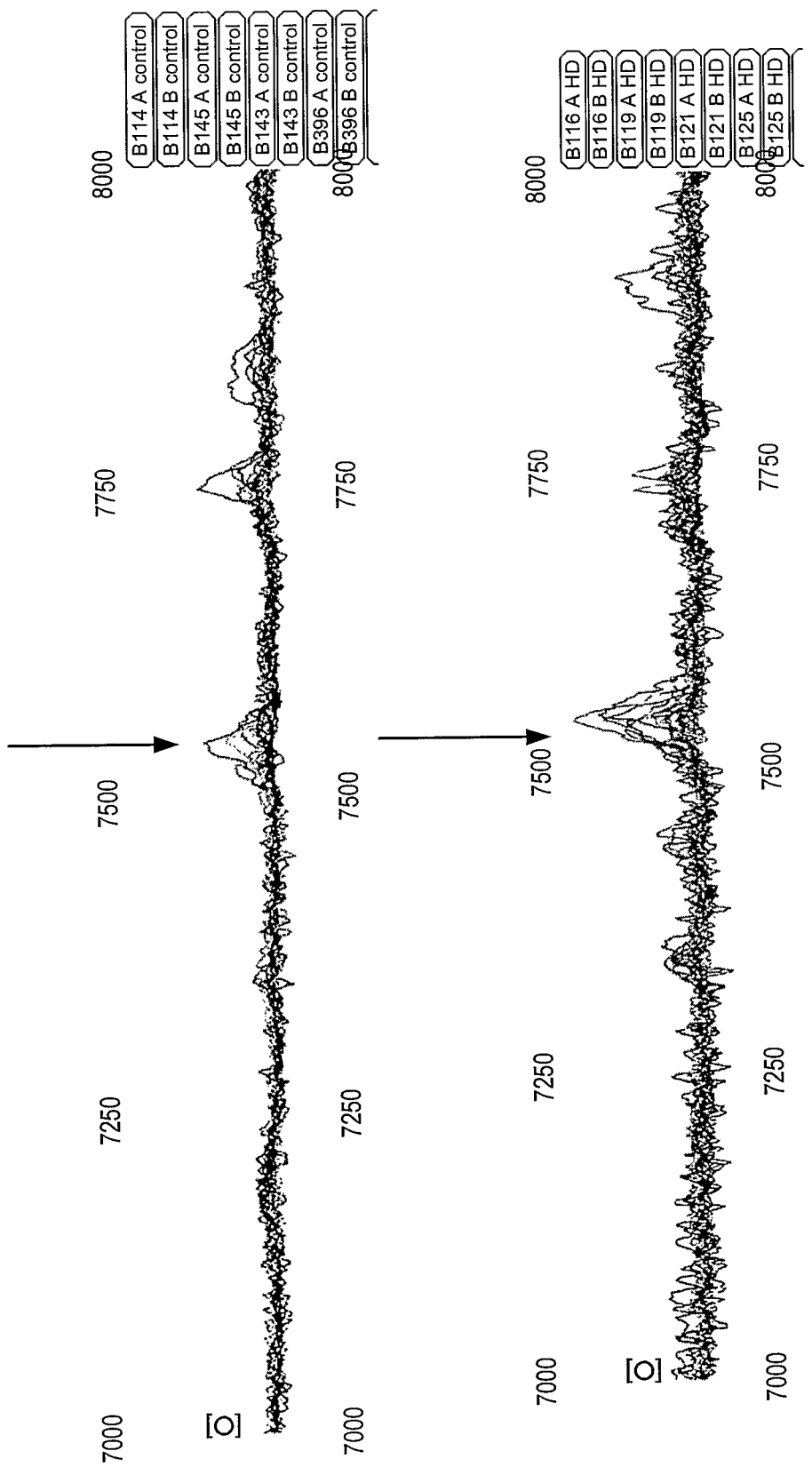
Figure 10:
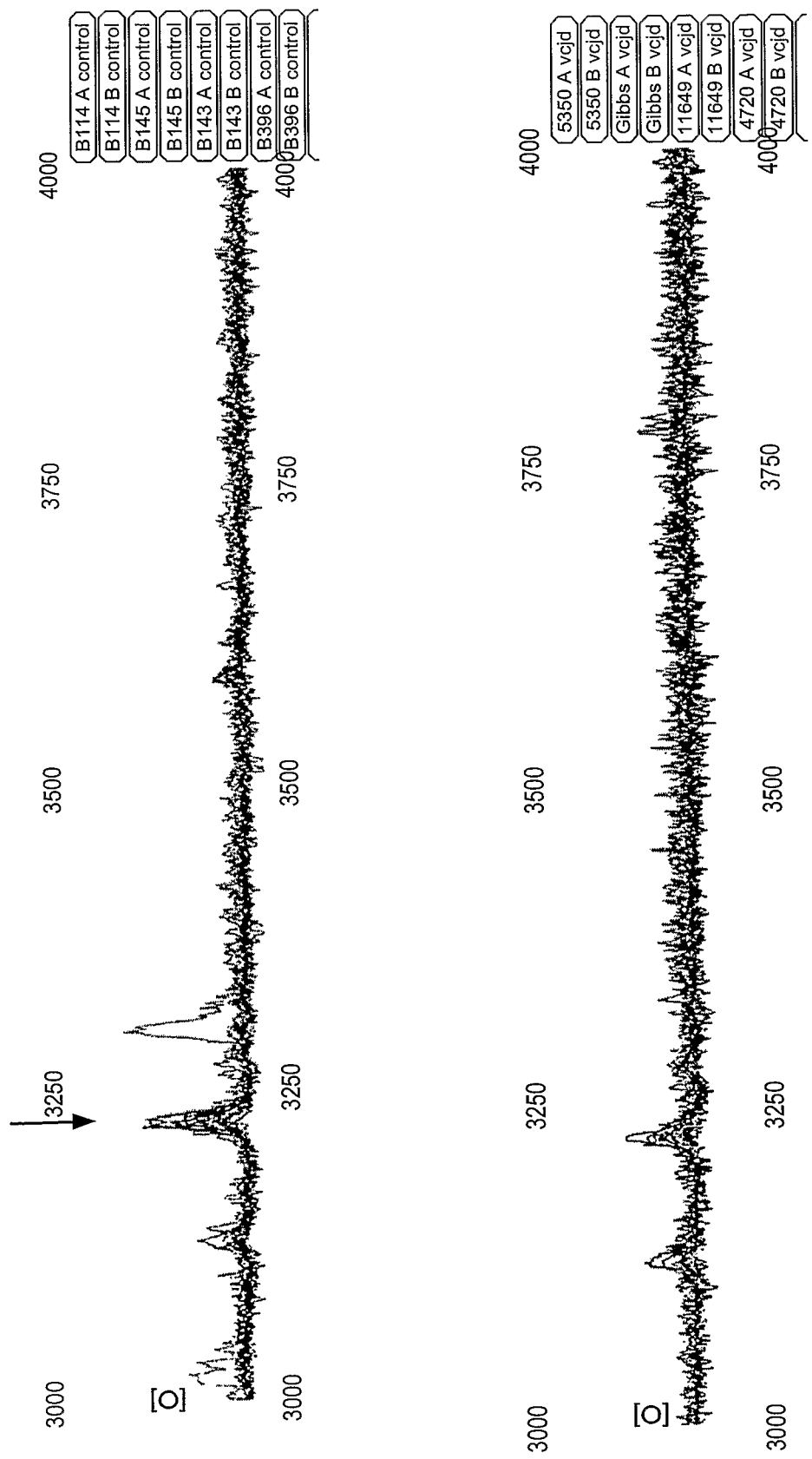
Figure 11:
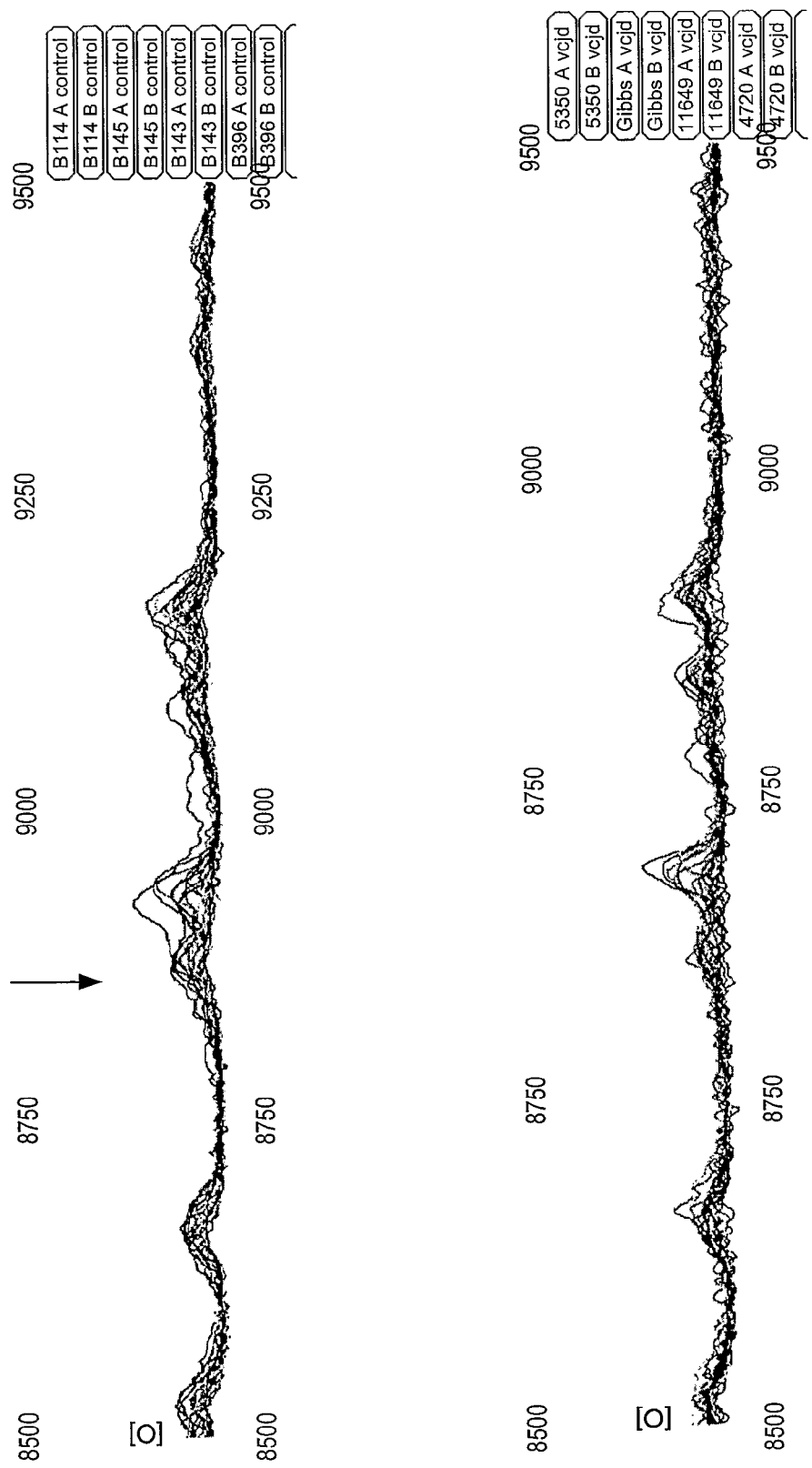
Figure 12:
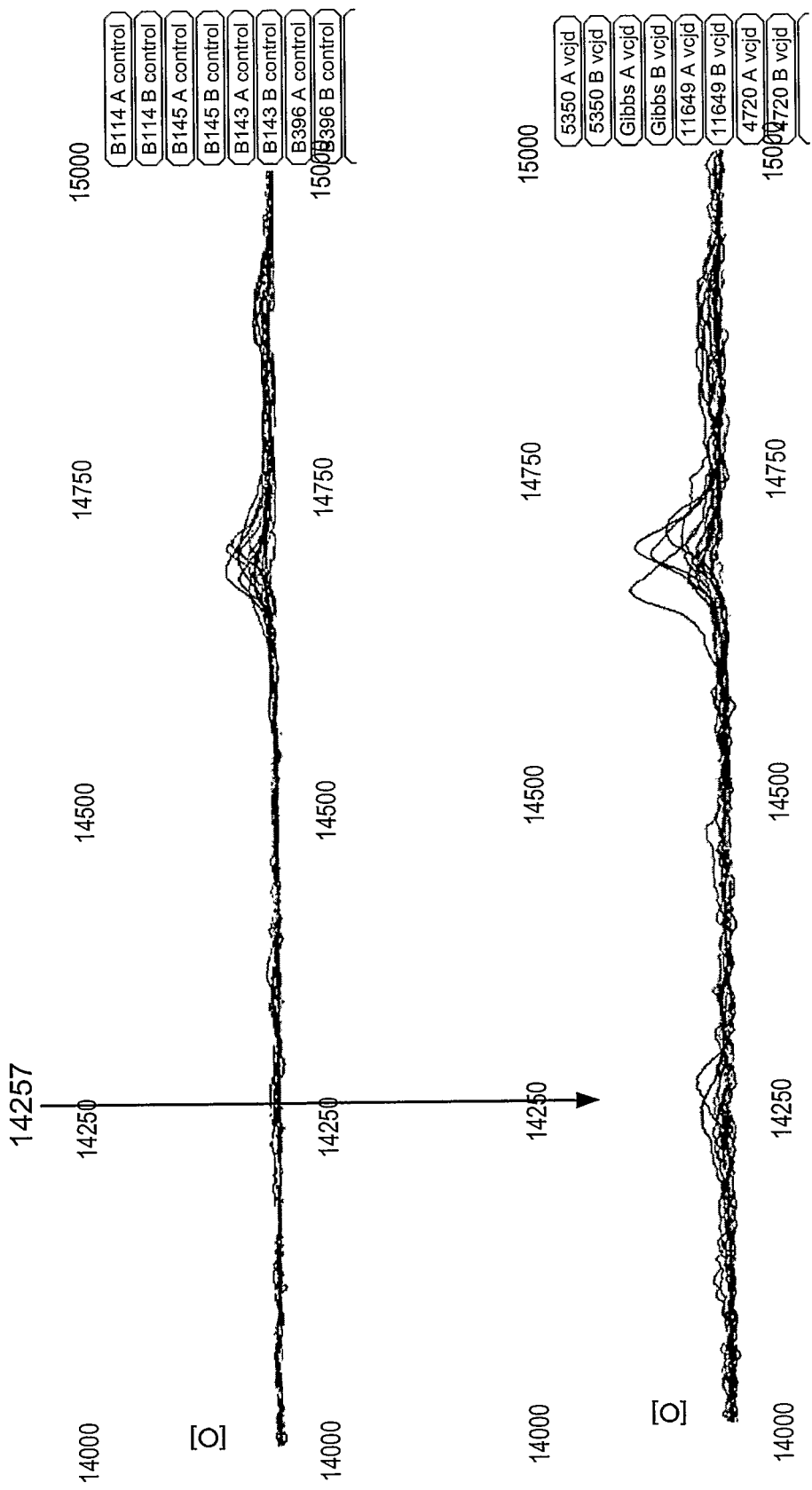
Figure 13:
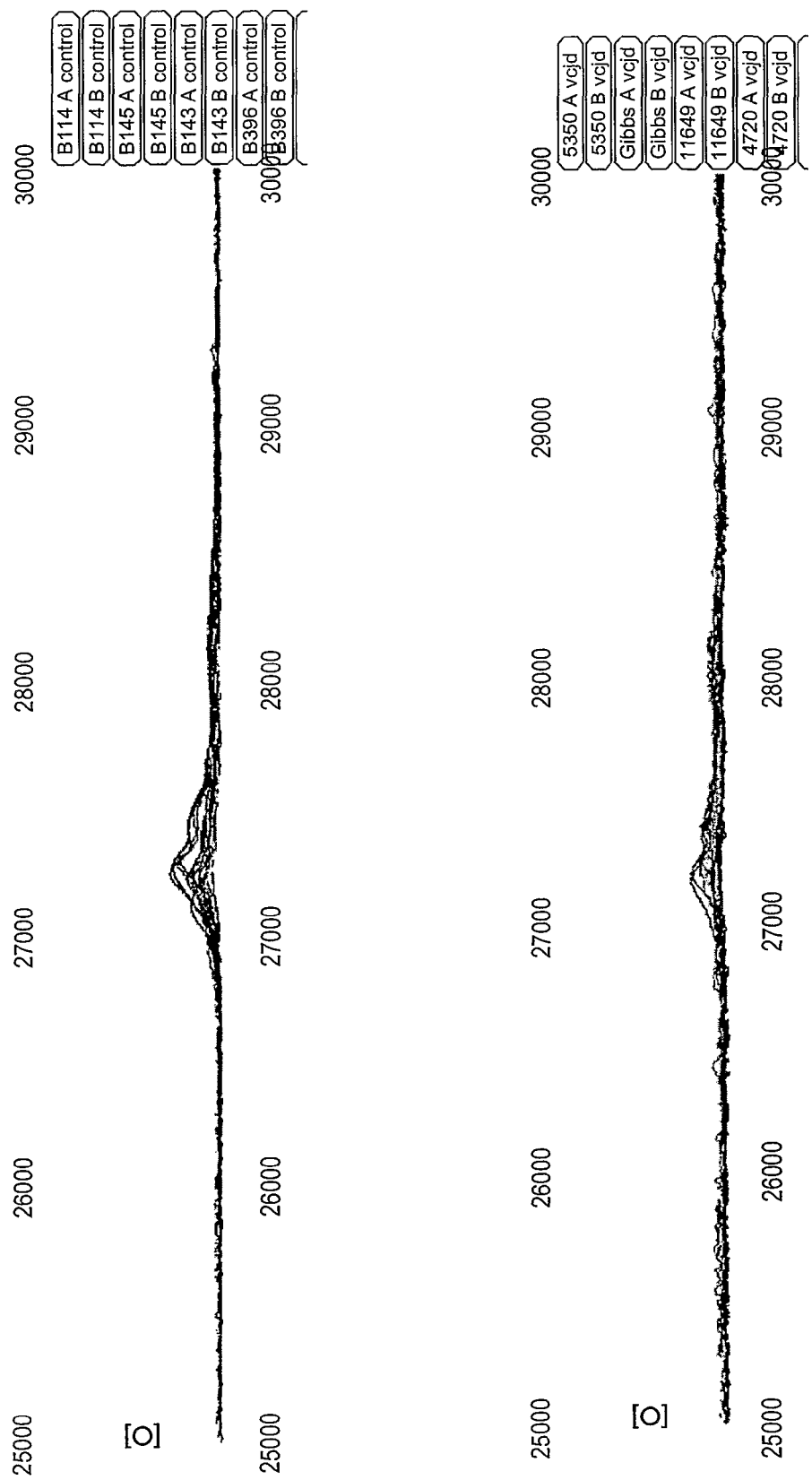

SELDI traces for the depleted plasma Q10 SAX2 dataset are shown in FIGS. 6 and 7. FIG. 6 shows SELDI spectra showing peaks in the region of m/z 4100-4500. FIG. 7 shows SELDI spectra showing peaks in the region of m/z 8600-9400. The upper and lower panels show overlayed spectra belonging to the control (CTRL) and vCJD groups, respectively. Asterisks (*) mark the peaks of interest.

SELDI traces for the undepleted plasma CM10 WCX dataset are shown in FIGS. 8 to 13.

1.4 SELDI Data Analysis

The data analysis approach adopted for this study comprises several modules as described below. To be considered as a candidate of interest, each biomarker must satisfy the following three criteria, the values of which are derived either from the multivariate modelling process or univariate tests.

The position of the peak of interest within the loadings plot indicates an obvious contribution to the separation of the groups in the data modelling process and this also survives a cross validation exercise.

A p value of <0.05 is achieved using a Mann-Whitney univariate test.

The magnitude of change in abundance of the marker between two groups is >1.5 fold either up or down regulated.

Pre-Processing:

All data were imported to the SIMCA-P software package (Umetrics). Variables corresponding to masses below m/z 2,500 were excluded due to the considerable chemical noise in this region. The remaining variables corresponding to masses between m/z 2,500 and m/z 100,000 were centered to the mean value and Pareto scaled.

Principal Component Analysis (PCA):

PCA models were fitted to the data sets with as many components (A) as would fit following the internal rules SIMCA-P uses to determine the significance of the components (Eriksson et al. 2001). The goodness of fit ($R^2$) and goodness of prediction ($Q^2$) parameters were used to assess the usefulness of each of the subsequent components fitted in the model. The automatically fitted components were inspected and kept as long as the $Q^2$ parameter was increasing. The cumulative $R^2$ parameter for the final accepted component gave the total proportion of variance in the data explained by the model. Plots were produced displaying the observation scores (t) and variable loadings (p) for pairs of principal components (a). The scores plots were inspected to look for patterns of systematic variation and outlying observations that could hamper later classification efforts. In particular, the positions of observations analysed on each chip were scrutinised to check for unusual chips. The reproducibility of duplicated sample analyses were also checked using the scores plots. The Ellipse shown on the scores plots corresponds to Hotelling's $T^2$ at 95%, a multivariate adaptation of a confidence region. For a data set with a multivariate normal distribution, 95% of the observations would be expected to lie within the region encompassed by the Ellipse, thus observations that are a long way outside the ellipse may represent problems to be investigated and addressed.

Trends found through inspection of the scores plots were interpreted through inspection of the variables found on the corresponding loadings plots. Individual m/z values plotted at the extremes of the plot were considered to be most influential on the separation of the groups. Interestingly, such plots tend to show several consecutive m/z datapoints, which effectively describe the original peak observed in the SELDI profiles themselves.

Partial Least Squares Data Analysis (PLS-DA) and Modelling:

Components (A) of PLS-DA models were fitted to the data sets as long as they met the criteria used by SIMCA-P to determine the significance of components (Eriksson et al. 2001). As for the PCA modelling, the $R^2$ and $Q^2$ parameters were inspected to determine which components should be included in the model. Unlike the PCA modeling, PLS-DA models posses $R^2$ values describing the fit of the model to both the X (measurement) variables and the Y (class) variables. Plots were produced displaying the observation scores (t) and the variable weights (w*c) for pairs of PLS components (a). Because each PLS component is fitted so as to both approximate the X and Y data well and maximize the correlation between the X and Y data, in practice the first one or two components usually separate the observations well when there are few groups present in the data set. The interpretation of the PLS scores and weights plots is similar to that used to interpret a PCA model, with the PLS weights being analogous to the PCA loadings. Hotelling's $T^2$ was computed and displayed on all PLS scores plots to help identify deviating observations.

The two parameters referred to as variable influence on projection (VIP) and PLS coefficients (COEFF) were used to determine which of all the masses measured in the SELDI spectral data were most important in defining the model parameters and explaining the groups. Specific thresholds were determined empirically and used to exclude those variables with VIP and COEFF values lower than the threshold. The ability of the PLS-DA models generated to correctly predict the class of (new) samples was determined by 2-fold cross-validation. Cross-validation was performed by dividing the data set into a training and a test set. A PLS-DA model was fitted to the training portion of the data set and subsequently used to predict the classes of the test portion of the data set. The training and test data sets were then swapped and the process repeated. The number of correct and incorrect classifications from both rounds of testing were recorded and used to calculate sensitivities and specificities of the predictions. This cross-validation method was used to test both the models built using the data set containing all variables and those built following variable selection (as described above).

Univariate Methods:

Statistical significance testing was performed using the Protein Chip software (Ciphergen Biosystems). Mann-Whitney (Wilcoxon) tests for two independent samples were used. Peak detection and matching were performed using the Protein Chip software and this data was then submitted to the Biomarker Wizard module for analysis. The p-value was taken as the result of the test. The data for each of the marked peaks was also exported to Excel (Microsoft) as peak intensities to calculate the fold change criteria for each peak. Because of the skewed distributions observed for the areas or intensities of each set of matched peaks, the data were $\log_{10}$ transformed prior to calculation of the mean and median values of the distributions as well as the standard deviations. The parameters of the distributions were then transformed back onto the original scales in order to calculate fold-changes and effect sizes. Fold-changes were calculated by dividing the larger of the mean (or median) values by the smaller value of two groups, yielding a value greater than or equal to one. Effect size (Cohen's D) was calculated as the difference between the mean values of two groups divided by the pooled standard deviation.

1.5 Candidate Identification

Having produced/created a list of candidate peaks of interest corresponding to each chip surface, the identity of the proteins responsible for each discriminating peak was determined.

Material was extracted directly from the chip surface and following electrophoretic separation and enzymatic digestion proteins were identified by electrospray tandem mass spectrometry (LC/MS/MS).

There are several advantages inherent to this strategy:
Pooling of material from several target positions overcomes challenges working with low level of protein and increased sensitivity is achieved.

SDS-PAGE provides an additional stage of visualisation of the sample as well as serving as an important separation and concentration step.

LC/MS/MS of digested proteins is routine methodology in our laboratory.

Bands of interest were excised from the silver stained gel and "in-gel" reduction, alkylation and digestion with trypsin were performed prior to subsequent analysis by LC/MS/MS. Peptides were extracted from the gel pieces by a series of acetonitrile and ammonium bicarbonate washes. The extract was pooled with the initial supernatant and lyophilised. Each sample was then resuspended in 23 µl of 50 mM ammonium bicarbonate. Chromatographic separations were performed using an Ultimate LC system (Dionex, UK). Peptides were resolved by reversed phase chromatography on a 75 µm C18 PepMap column. A gradient of acetonitrile in 0.05% formic acid was delivered to elute the peptides at a flow rate of 200 nl/min. Peptides were ionised by electrospray ionisation using a Z-spray source fitted to a QTof-micro (Waters Corp.). The instrument was set to run in automated switching mode, selecting precursor ions based on their m/z and intensity, for sequencing by collision-induced fragmentation.

The mass spectral data was processed into peak lists (containing the precursor ion m/z and charge state and the m/z and intensity of the fragment ions. Database searching was undertaken to establish the identity of the protein(s) present. This was performed using the Mascot search algorithm against the NCBI non-redundant (nr) and SWISS-PROT databases.

Once proteins were identified the expected molecular weight of the mature proteins was extrapolated from the information contained within the database entry and correlated with the molecular weight determined experimentally in the original SELDI profiles. In this way it was possible in most cases to assign related species to a single protein sequence.

2.1 SELDI Data Analysis

Following extensive analysis using multivariate techniques and Mann-Whitney tests, the depleted plasma study (Q10 SAX chip) revealed variation in several peaks, which discriminate between vCJD and control samples (see Table 3 below). Similarly, for undepleted plasma the CM10 WCX profiles reveal additional discriminatory peaks (see Table 4 below).

TABLE 3

SELDI peaks of interest discriminating between vCJD and control samples (depleted plasma study using Q10 SAX chip)

| Candidate Reference number | Peak of Interest | p-value[a] | Fold-Change (mean)[b] | Fold-change (median)[c] | Direction of change | Cohen's D[d] |
|---|---|---|---|---|---|---|
| P1 | 8644 | 0.023 | 2.47 | 3.19 | Decreased | 1.130 |
| P2 | 8856 | 0.045 | 1.75 | 1.95 | In CJD | 0.934 |
| P3 | 4132 | 0.001 | 3.87 | 5.16 | Increased | 1.743 |
| P4 | 4340 | 0.011 | 1.85 | 1.93 | in CJD | 1.136 |
| P5 | 4490 | 0.023 | 1.69 | 1.76 |  | 0.990 |

TABLE 4

SELDI peaks of interest discriminating between vCJD and control samples (undepleted plasma study using CM10 WCX chip)

| Candidate Reference number | Peak of Interest | p-value[a] | Fold-Change (mean)[b] | Fold-change (median)[c] | Direction of change | Cohen's D[d] |
|---|---|---|---|---|---|---|
| P6 | 3223 | 0.009 | 1.50 | 1.50 | Decreased | -1.300 |
| P7 | 8868 | 0.023 | 1.60 | 1.20 | In CJD | -2.100 |

TABLE 4-continued

SELDI peaks of interest discriminating between vCJD and control samples (undepleted plasma study using CM10 WCX chip)

| Candidate Reference number | Peak of Interest | p-value[a] | Fold-Change (mean)[b] | Fold-change (median)[c] | Direction of change | Cohen's D[d] |
|---|---|---|---|---|---|---|
| P8 | 27202 | 0.037 | 1.50 | 1.50 |  | -1.500 |
| P9 | 6243 | 0.023 | 1.50 | 1.50 | Increased | 3.000 |
| P10 | 7533 | 0.003 | 2.40 | 2.40 | in CJD | 1.900 |
| P11 | 14257 | 0.028 | 1.80 | 1.70 |  | 0.900 |

Notes:
[a]p-values computed for a Mann-Whitney test (not corrected for multiple testing).
[b]Mean and median peak intensity values for each group were estimated after $log_{10}$ transformation of the data. The estimates were transformed back to the original scale prior to calculating fold-changes.
[c]The effect size (Cohen's D) is computed as the different between the means divided by the pooled standard deviation.

2.2 Candidate Identification

Figure 14:
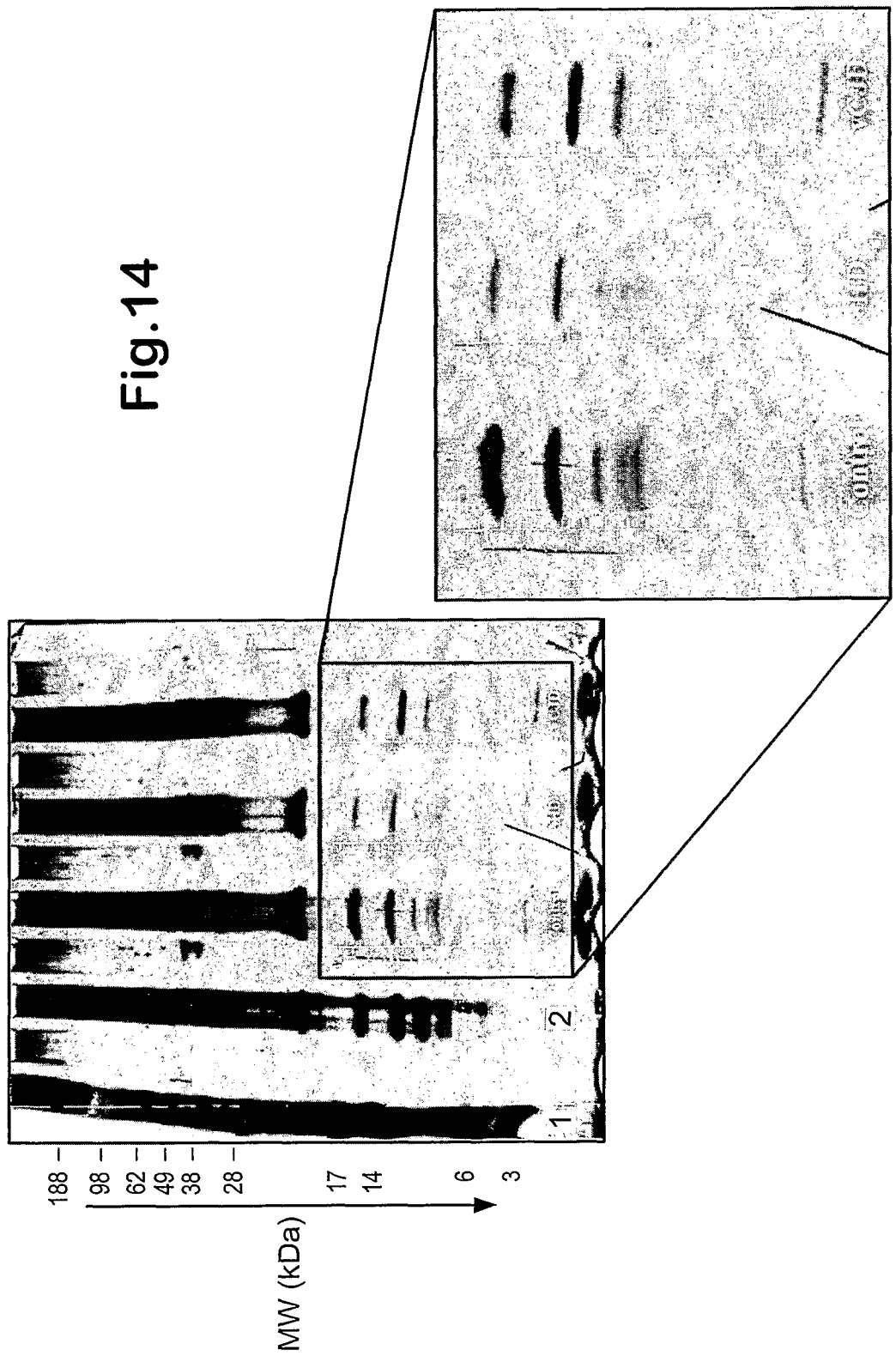
FIG. 14 is an image of a silver stained gel of the material extracted from depleted plasma Q10 chips, as described in Example 2.

The silver stained gel of the material extracted from the depleted plasma Q10 chips is shown in FIG. 14. Although a total of 36 sections were excised, we considered 9 sections to be important to the key objective of the identification of the proteins responsible for the peaks indicated in Table 3. Hence, we gave priority to the LC/MS/MS analysis of these particular bands namely bands 2, 3, 4, 5, 7 and 8 from the control lane and bands 9, 10 and 11 from the vCJD lane. A summary of the results is given in Table 5. Similarly, LC/MS/MS was also undertaken on material extracted from the CM10 WCX chip. The silver stained gel of the material extracted from the depleted plasma WCX CM10 chips is shown in FIG. 15 and the proteins identified in the analyses are shown in Table 6.

TABLE 5

Summary of LC/MS/MS results for Bands extracted from the Q10 chips

| Band# | Experimental Mr (kDa) | Protein ID | Swiss Prot Accession # | Mr indicated in database entry (kDa)* |
|---|---|---|---|---|
| 2 | 12 | Transthyretin | P02766 | 15.8 |
| 3 | 10 | Haptoglobin | P00738 | 45.1 |
| 4 | 9 | Apolipoprotein C-III | P02656 | 10.8 |
| 5 | 8 | Apolipoprotein C-III | P02656 | 10.8 |
| 7 | 10 | Vitronectin precursor | P04004 | 54.2 |
|  |  | Hemoglobin beta chain | P02025 | 15.8 |
| 8 | 6 | Apolipoprotein C-III | P02656 | 10.8 |
| 9 vCJD | 5 | Not yet established | — | — |
| 10 vCJD | 4-5 | Not yet established | — | — |
| 11 vCJD | 3 | Not yet established | — | — |

Note:
*The molecular weights indicated in Swiss Prot generally refer to the precursor proteins rather than the mature proteins, which exist after processing. Please also note that further interpretation of the LC/MS/MS data for Bands 9, 10 and 11 may reveal the presence of unexpected proteolytic fragments.

TABLE 6

Summary of LC/MS/MS results for Bands extracted from the CM10 chips

| Band# | Experimental Mr (kDa) | Protein ID | Swiss Prot Accession # | Mr indicated in database entry (kDa)* |
|---|---|---|---|---|
| 1 + 6 | 27 | IgG lambda chain C | P01842 | 11 |
| 14-16 | 17-23 | IgG kappa chain C | P01834 | 11 |
|  |  | Serum Albumin | P02768 | 69 |
| 32-34 | 17-23 | IgG kappa chain C | P01834 | 11 |
|  |  | Apolipoprotein A-1 | P02647 | 30 |
| 19-21 | 12-14 | Serum Albumin | P02768 | 69 |

TABLE 6-continued

Summary of LC/MS/MS results for Bands extracted from the CM10 chips

| Band# | Experimental Mr (kDa) | Protein ID | Swiss Prot Accession # | Mr indicated in database entry (kDa)* |
|---|---|---|---|---|
| 37-39 | 12-14 | Serum Albumin | P02768 | 69 |
| 22-24 | 9-12 | Serum Albumin | P02768 | 69 |
|  |  | Apolipoprotein C-III | P02656 | 10 |
| 40-42 | 9-12 | Actin | P62736 | 41 |
| 3 + 8 | 9 | Serum Albumin | P02768 | 69 |
| 4 + 9 | 9 | Serum Albumin | P02768 | 69 |
| 5 + 10 | 3 | Serum Albumin | P02768 | 69 |
|  |  | alpha-Fetuin | P02765 | 39 |

The results suggest that a collection of human albumin fragments exist in the SELDI profiles and that these differ in abundance when vCJD cases are compared to controls. It is apparent that these relate to the N terminal region of the protein in particular. We therefore claim that six candidate peaks are related to N-terminal fragments of Human albumin and the basis of this claim is illustrated in Table 7 below.

TABLE 7

List of Candidate biomarkers matched to fragments within the N-terminal region of Human Albumin

| Candidate Ref# | $[M + H]^+$ observed m/z | Expected Average Mr | Residues | % Error |
|---|---|---|---|---|
| P1 | 8644 | 8642 | 2-78 | 0.020 |
| P2 | 8856 | 8857 | 2-80 | 0.010 |
| P3 | 4132 | 4130 | 41-78 | 0.050 |
| P4 | 4340 | 4344 | 41-80 | 0.090 |
| P11 | 14257 | 14255 | 5-129 | 0.010 |
| P8 | 27202 | 27206 | 6-242 | 0.015 |

The sequence of Human Albumin precursor was retrieved from the Swiss Prot database (P02768) and exported into the Biolynx software package within MassLynx for examination. The Mature albumin sequence is created by removing the first 18 amino acids as the signal peptide as well as a further 5 amino acids which relate to a pro peptide sequence. The residue numbers indicated refer to the mature protein of 585 amino acids in total. Each observed average Mr value is within 0.1% mass error of the predicted value.

For Hemoglobin beta chain (P02025) we can match a fragment extending from residues 4-43 to the peak at m/z 4490 (P5) and this encompasses two peptides observed in the LC/MS/MS data. These results are summarised below. Therefore we claim that candidate reference number P5 is likely to be residues 4-43 of Hemoglobin beta chain.

The potential processing of Hemoglobin beta chain is shown as follows:

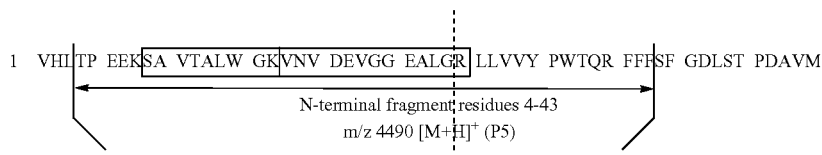

The amino acid sequence of Hemoglobin beta chain is shown with the location of potential fragment, residues 4-43 (P5), indicated by the arrow. The box indicates the location of the peptides observed in the LC/MS/MS data.

Each of the above-cited publications and database references is herein incorporated by reference to the extent to which it is relied on herein.

The invention claimed is:
1. A method comprising:
providing a blood, serum, or plasma sample from a human subject;
subjecting the sample to two dimensional gel electrophoresis to yield a stained gel; and
quantifying an increased or decreased concentration of each of a plurality of proteins in the sample, compared with a sample of a control, normal human subject, the plurality of proteins having an increased concentration being selected from the group consisting of:
beta-actin (SwissProt Acc. No. P60709);
apolipoprotein A-IV precursor (SwissProt Acc. No. P06727);
haptoglobin beta-chain consisting of residues 162-406 (SwissProt Acc. No. P00738);
hemoglobin beta chain (SwissProt Acc. No. P02023); and
alpha-1-antitrypsin (SwissProt Acc. No. P01009); and
the plurality proteins having a decreased concentration being selected from the group consisting of:
plasma protease (C1) inhibitor precursor (SwissProt Acc. No. P05155);
complement component 1, s sub-component (SwissProt Acc. No. P09871);
butyrylcholinesterase precursor (SwissProt Acc. No. P06276);
complement component C4B (SwissProt Acc. No. P01028);
lumican (SwissProt Acc. No. P51884);
alpha-fibrinogen precursor (SwissProt Acc. No. P02671);
IGHG4 protein (Swiss Prot Acc. No. Q8TC63); and
immunoglobulin lambda heavy chain,
wherein the increased or decreased concentration of each of the plurality of proteins is detected by an increased or decreased intensity of a protein-containing spot on the stained gel, compared with a corresponding control gel.
2. The method according to claim 1, wherein the detecting step further comprises performing on the sample a binding assay for the protein.
3. The method according to claim 2, wherein the binding assay comprises causing the protein of the sample to interact with a specific binding partner and detecting the interaction.
4. The method according to claim 3, wherein the labelled specific binding partner is a labelled antibody that recognizes the protein.
5. The method according to claim 1, wherein at least one of the plurality of proteins detected is an increased intensity of haptoglobin beta chain, Hemoglobin beta chain, or alpha-1-antitrypsin; or a decreased intensity of alpha-fibrinogen precursor, IGHG4 protein, or Immunoglobulin lambda heavy chain.

6. The method of claim 1, wherein samples taken at intervals from the same subject are quantified.

7. The method of claim 1, wherein the diagnostic sample is depleted of albumin and IgG before subjecting the diagnostic sample to two dimensional gel electrophoresis.

8. The method of claim 7, wherein the tissue is plasma.

9. The method of claim 1, comprising analyzing spots from the stained gel using liquid chromatography and mass spectrometry.

10. The method of claim 8, wherein the mass spectrometry is SELDI mass spectrometry.

* * * * *